United States Patent
den Hoed

(10) Patent No.: US 9,427,454 B2
(45) Date of Patent: Aug. 30, 2016

(54) METHOD OF MAKING LIQUID OLIVE LEAF EXTRACT

(71) Applicant: Robert den Hoed, Sioux Center, IA (US)

(72) Inventor: Robert den Hoed, Sioux Center, IA (US)

( * ) Notice: Subject to any disclaimer, the term of this patent is extended or adjusted under 35 U.S.C. 154(b) by 437 days.

(21) Appl. No.: 14/190,338

(22) Filed: Feb. 26, 2014

(65) Prior Publication Data

US 2015/0238554 A1 Aug. 27, 2015

(51) Int. Cl.
*A61K 36/63* (2006.01)

(52) U.S. Cl.
CPC ........... *A61K 36/63* (2013.01); *A61K 2236/00* (2013.01)

(58) Field of Classification Search
CPC ..................................................... A61K 36/63
USPC ................................................. 424/769, 774
See application file for complete search history.

(56) References Cited

U.S. PATENT DOCUMENTS

| | | | | |
|---|---|---|---|---|
| 5,714,150 A * | 2/1998 | Nachman | ............... | A61K 36/63 424/769 |
| 8,535,737 B2 * | 9/2013 | Tieu | ............... | A61K 36/28 424/725 |
| 2006/0276545 A1 * | 12/2006 | Biessen | ............... | A61K 9/107 514/563 |
| 2008/0108587 A1 * | 5/2008 | Yoshimura | ............ | A61K 31/05 514/62 |
| 2008/0146828 A1 * | 6/2008 | Benavent | ............... | C05F 5/006 554/177 |
| 2008/0187620 A1 * | 8/2008 | Nielsen | ............... | A61K 36/63 426/2 |
| 2010/0324343 A1 * | 12/2010 | Breuninger | ........... | C07C 37/002 568/764 |
| 2011/0142973 A1 * | 6/2011 | Lee-Huang | ............ | A61K 31/05 424/774 |
| 2013/0101627 A1 * | 4/2013 | Tieu | ............... | A61K 36/28 424/278.1 |
| 2013/0272974 A1 * | 10/2013 | Alkayali | ............... | A61K 8/347 424/59 |

FOREIGN PATENT DOCUMENTS

| | | | |
|---|---|---|---|
| CN | 102701914 A | * | 10/2012 |
| CN | 103709014 A | * | 4/2014 |
| EP | 1795201 A1 | * | 6/2007 |

* cited by examiner

*Primary Examiner* — Chris R Tate
(74) *Attorney, Agent, or Firm* — Zarley Law Firm, P.L.C.

(57) ABSTRACT

A method of making liquid olive leaf extract that includes the mixing ground olive leaf, water, and an acid in a container. Once mixed heating the mixture a predetermined temperature for approximately four hours. Next raising the pH to approximately 4.0 and then adding a predetermined amount of cellulase and invertase to the mixture. Then the mixture is mixed for a predetermined period of time. After mixing, sediment is remove from the mixture and the pH is adjusted to approximately 3.0. The mixture is then reduced to a concentrate.

11 Claims, 2 Drawing Sheets

METHOD OF MAKING LIQUID OLIVE LEAF EXTRACT

BACKGROUND OF THE INVENTION

This invention is directed to a method of making olive extract. More particularly, this invention is directed to a method of making liquid olive leaf extract.

The use of olive leaf extract is old and well known as a substance to have healing properties. Olive leaf extract lends itself as a multi-functional alternative treatment for many diseases and conditions. The chemical compound oleuropein ($C_{25}H_{32}O_{13}$) tyrosol and hydroxytyrosol, and more particularly the active ingredient elenolic acid, found in olive extracts has antiviral, antifungal, and antibacterial properties thereby making it effective in fighting a wide range of diseases including: influenza, common cold, bacterial/viral meningitis, postsurgical infections, kidney infections, shingle, hepatitis, pneumonia, malaria.

Additionally, olive leaf extract can be used as a disease preventative. For instance, oleuropein and its derivatives such as tyrosol and hydroxytyrosol have anti-hypertensive properties making it an effective way to reduce the risk of heart disease. Further, it has been found to prevent muscle spasm related to irritable bowel syndrome. Olive leaf extract also has antioxidant qualities that make it effective against peroxyl radicals, hydroxyl radicals, peroxynitrite, and super oxide anions.

Given the wide range of health benefits offered by olive leaf extract, a low-cost and efficient method of extracting the leaf extract is needed. Current methods fail to adequately remove sediment and maximize extraction.

Thus it is a primary object of the invention to provide a method of making liquid olive leaf extract that improves upon the state of the art.

Another object of the invention is to provide a low-cost method that maximizes extraction.

Yet another object of the invention is to provide a simple method that limits the number of substances needed to achieve extraction.

These and other object, features, or advantages of the present invention will become apparent from the specification and claims.

SUMMARY OF THE INVENTION

A method of making liquid olive leaf extract that includes the mixing ground olive leaf, water, and an acid in a container. Once mixed heating the mixture a predetermined temperature for approximately four hours. Next raising the pH to approximately 4.0 and then adding a predetermined amount of cellulase and invertase to the mixture. Then the mixture is mixed for a predetermined period of time. After mixing, sediment is remove from the mixture and the pH is adjusted to approximately 3.0. The mixture is then reduced to a concentrate.

DETAILED DESCRIPTION OF THE PREFERRED EMBODIMENTS

Figure 1:
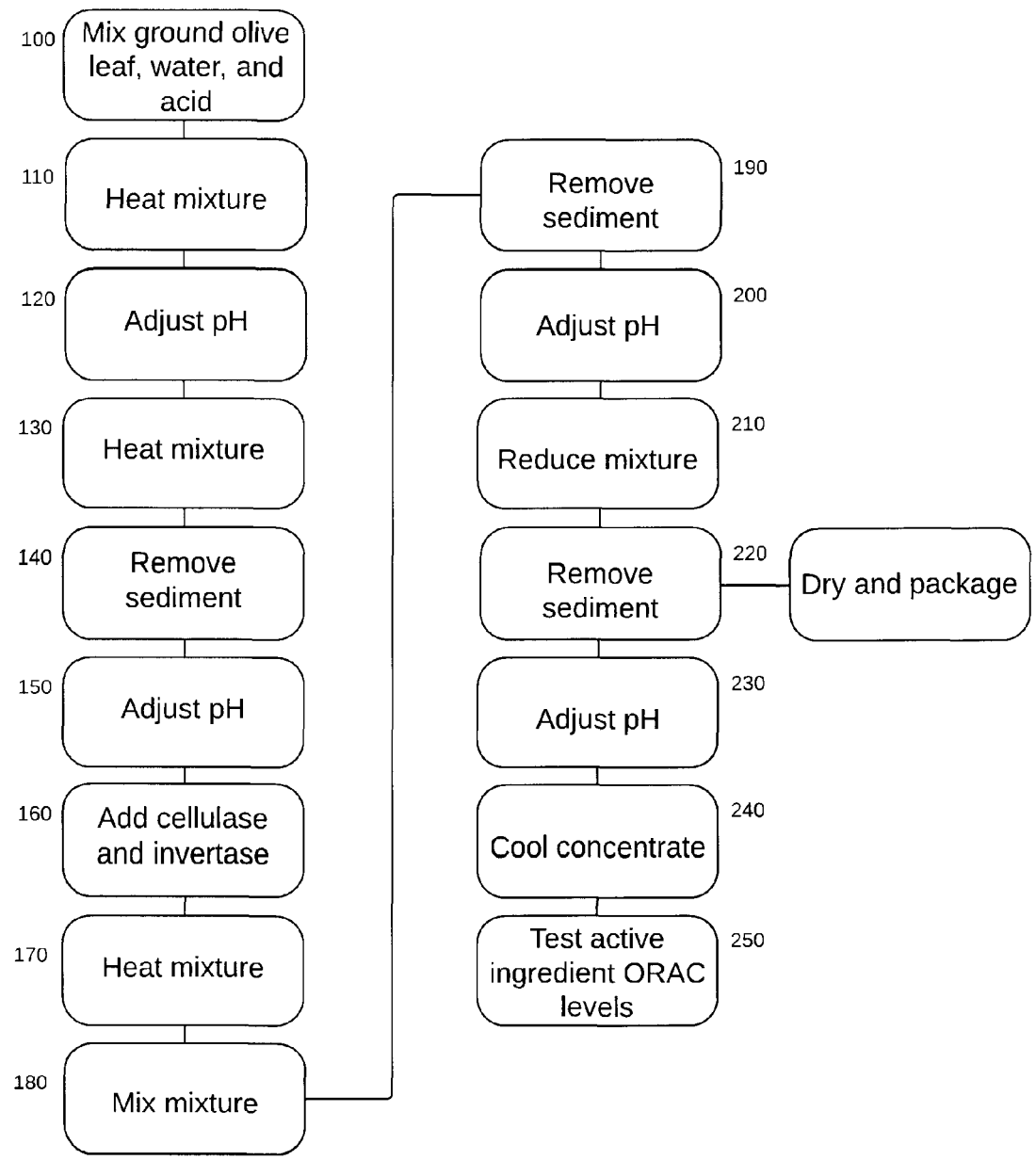
FIG. 1 is a flow diagram of a method of making liquid olive leaf extract.
Figure 2:
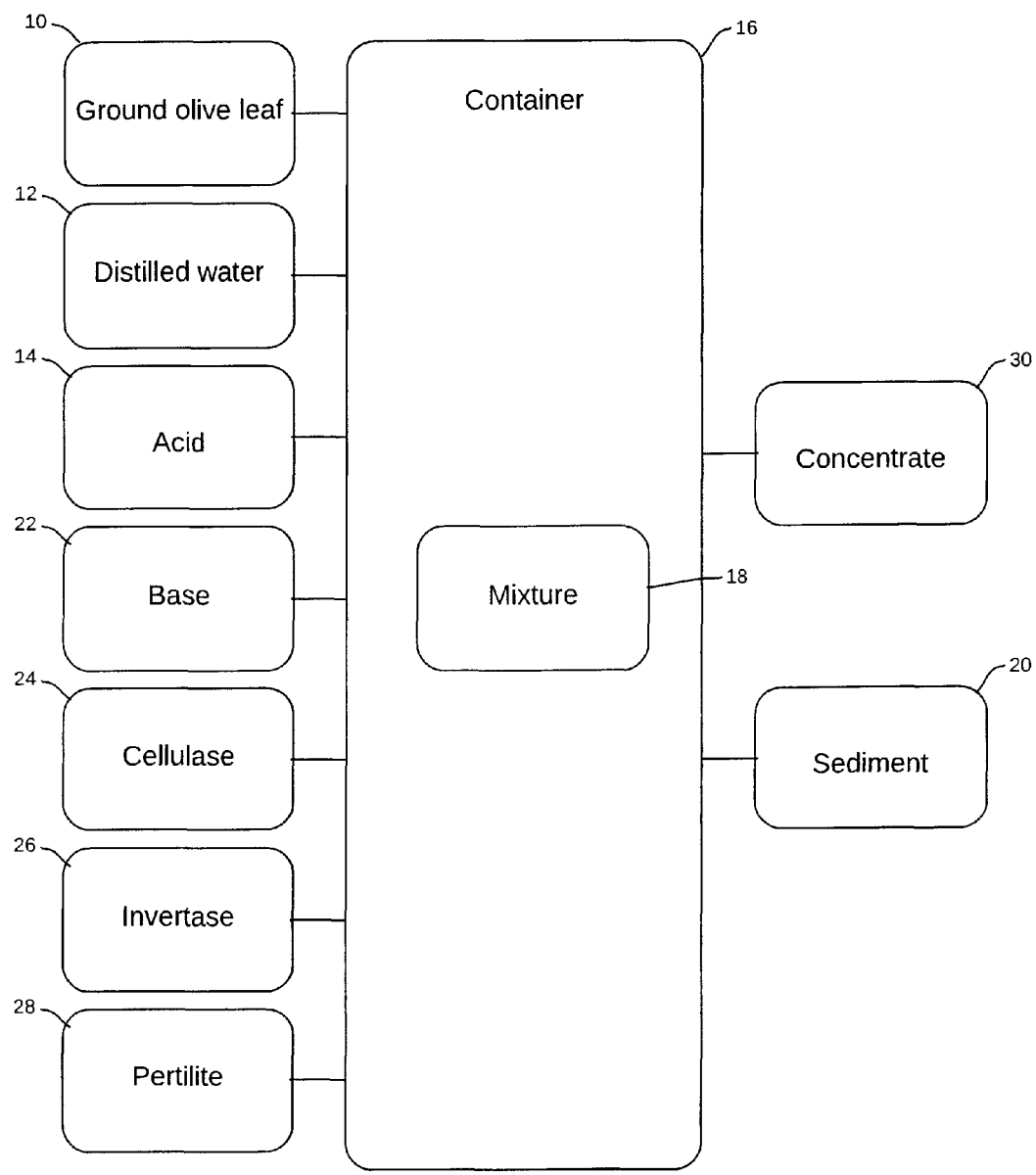
FIG. 2 is a schematic drawing of an environment of making liquid olive leaf extract.

Referring to the Figures, a method of making liquid olive leaf extract begins at step 100 by mixing ground olive leaf 10, distilled water 12, and an acid 14, such as hydrochloric acid, in a container 16 to form a mixture 18. For example, 744 grams of ground olive leaf 10 are mixed with 11.34 liters of distilled water 12. Then a sufficient amount of hydrochloric acid 14 is added to bring the pH of the mixture 18 to between 2.50 and 3.75, and preferably 3.0.

The mixture 18 is then heated at step 110 to between 40° C. and 80° C., and preferably 60° C. As the mixture 18 is heated, the pH level of the mixture 18 is adjusted at step 120 to maintain the desired pH level by adding hydrochloric acid 14. Once the desired temperature is reached the mixture 18 continues to be heated for approximately four hours at step 130.

Next, at step 140, sediment 20 is removed from the mixture 18 either by filtering or centrifuging the mixture 18. Once the sediment 20 is removed, a base 22, such as sodium hydroxide, is added to the mixture at step 150 to bring the pH level to approximately 4.0. At step 160, between 0.1 and 100 grams of cellulase 24 and invertase 26 are also added to the mixture 18. Preferably, 10.5 grams of each are added to the mixture 18. The mixture 18 is then heated at step 170 to approximately 55° C. At step 180 the mixture 18 mixed for between 1 and 48 hours, and preferably 10 hours.

Upon completion, at step 190 sediment 20 is removed from the mixture 18 by using perilite 28 or centrifuging. Hydrochloric acid 14 is then added at step 200 to bring the pH level of the mixture 18 to approximately 3.0. The mixture 18 is reduced at step 210 to a concentrate 30 through evaporation at a temperature between 50° C. and 95° C., preferably 60° C.

Once the concentrate 30 is formed, the sediment 20 is again removed through filtering or centrifuging at step 220. The pH level is adjusted at step 230 to about 3.0 by adding hydrochloric acid 14. The concentrate 30 is then cooled or frozen at step 240. Finally, at step 250 the oxygen radical absorbance capacity (ORAC) levels of the concentrate 30 are measured in a lab.

What is claimed:

1. A method of making a concentrate of a liquid olive leaf extract comprising the steps of:
    mixing ground olive leaf, water, and an acid in a container to form a mixture having a pH between approximately 2.50 and 3.75:
    heating the mixture to a predetermined temperature for approximately 4 hours;
    raising the pH of the mixture to approximately 4.0;
    adding a predetermined amount of a combination of cellulase and invertase to the mixture;
    remixing the mixture for a predetermined period of time;
    removing sediment from the mixture;
    lowering the pH of the mixture to approximately 3.0; and
    reducing the mixture to form the concentrate.

2. The method of claim 1 wherein the concentrate contains oleuropein, tyrosol, and hydroxytyrosol.

3. The method of claim 1 wherein between 0.1 and 100 grams of the cellulase and invertase are added.

4. A method of making a concentrate of a liquid olive leaf extract comprising the steps of:
    mixing ground olive leaf, water, and an acid in a container to form a mixture having a pH between 2.50 and 3.75:
    heating the mixture to between 40° C. and 80° C. for approximately 4 hours;
    adding a base to the mixture to raise the pH of the mixture to approximately 4.0;
    adding between 0.1 to 100 grams of a combination of cellulase and invertase to the mixture;
    remixing the mixture for between 1 and 48 hours;

removing sediment from the mixture;
adding acid to the mixture to lower the pH of the mixture to approximately 3.0; and
reducing the mixture to form the concentrate.

5. The method of claim 4 further comprising the step of cooling the concentrate.

6. The method of claim 4 further comprising the step of testing the ORAC level of the concentrate to determine that the concentrate has an antioxidant level of 1-90 million ORAC units.

7. The method of claim 4 wherein the initial pH of the mixture is brought to 3.0.

8. The method of claim 4 wherein the acid is hydrochloric acid.

9. The method of claim 4 wherein the base is sodium hydroxide.

10. The method of claim 4 wherein the mixture is initially heated to 60° C.

11. The method of claim 4 wherein the mixture is reduced to a concentrate by evaporation.

* * * * *